United States Patent
Tepper et al.

(10) Patent No.: US 7,601,262 B1
(45) Date of Patent: Oct. 13, 2009

(54) SUB-MICRON FILTER

(75) Inventors: Frederick Tepper, Sanford, FL (US);
Leonid Kaledin, Port Orange, FL (US)

(73) Assignee: Argonide Corporation, Sanford, FL (US)

( * ) Notice: Subject to any disclaimer, the term of this patent is extended or adjusted under 35 U.S.C. 154(b) by 415 days.

(21) Appl. No.: 11/023,281

(22) Filed: Dec. 27, 2004

Related U.S. Application Data

(63) Continuation-in-part of application No. 10/177,709, filed on Jun. 21, 2002, now Pat. No. 6,838,005.

(60) Provisional application No. 60/300,184, filed on Jun. 22, 2001.

(51) Int. Cl.
*B01D 39/00* (2006.01)

(52) U.S. Cl. .................. 210/502.1; 55/527; 96/108; 210/503; 210/505; 502/407; 502/415

(58) Field of Classification Search ............. 210/263, 210/266, 503–509, 634, 639, 650, 651, 690, 210/691, 764, 767, 502.1; 55/527, 528; 95/273, 95/285; 423/627, 629, 111, 624; 516/94; 502/414, 415, 407; 131/333; 96/108
See application file for complete search history.

(56) References Cited

U.S. PATENT DOCUMENTS

| | | | |
|---|---|---|---|
| 2,773,601 A | 12/1956 | Keller et al. | |
| 2,783,894 A | 3/1957 | Lovell et al. | |
| 2,915,475 A * | 12/1959 | Bugosh | 516/94 |
| 2,917,426 A * | 12/1959 | Bugosh | 162/145 |
| 3,025,233 A * | 3/1962 | Figert | 210/502.1 |
| 3,031,417 A | 4/1962 | Bruce | |
| 3,031,418 A * | 4/1962 | Bugosh | 516/94 |

(Continued)

FOREIGN PATENT DOCUMENTS

DE 2410215 A 9/1974

(Continued)

OTHER PUBLICATIONS

Dicosmo, et al., (1994), Cell immobilization by adsorption to glass fibre mats, Immobilized Biosystems, Ed. by Veliky, I.A. and McLean, R.J.C., Blackie Academic & Professional.

(Continued)

*Primary Examiner*—Joseph W Drodge
(74) *Attorney, Agent, or Firm*—Alicia M. Passerin, Esq.; Cohen & Grigsby, P.C.

(57) ABSTRACT

Aluminum hydroxide fibers approximately 2 nanometers in diameter and with surface areas ranging from 200 to 650 m²/g have been found to be highly electropositive. When dispersed in water they are able to attach to and retain electronegative particles. When combined into a composite filter with other fibers or particles they can filter bacteria and nano size particulates such as viruses and colloidal particles at high flux through the filter. Such filters can be used for purification and sterilization of water, biological, medical and pharmaceutical fluids, and as a collector/concentrator for detection and assay of microbes and viruses. The alumina fibers are also capable of filtering sub-micron inorganic and metallic particles to produce ultra pure water. The fibers are suitable as a substrate for growth of cells. Macromolecules such as proteins may be separated from each other based on their electronegative charges.

8 Claims, 5 Drawing Sheets

U.S. PATENT DOCUMENTS

| | | | | |
|---|---|---|---|---|
| 3,117,944 | A * | 1/1964 | Harrell | 523/333 |
| 3,234,075 | A * | 2/1966 | Braitberg | 162/161 |
| 3,242,073 | A | 3/1966 | Guebert at al. | |
| 3,352,424 | A | 11/1967 | Guebert et al. | |
| 3,408,315 | A | 10/1968 | Piane | |
| 3,793,061 | A * | 2/1974 | Hammel et al. | 427/244 |
| 3,947,562 | A | 3/1976 | Grimshaw et al. | |
| 4,007,113 | A | 2/1977 | Ostreicher | |
| 4,007,114 | A | 2/1977 | Ostreicher | |
| 4,037,607 | A * | 7/1977 | Grossman | 131/333 |
| 4,059,119 | A | 11/1977 | Grossman | |
| 4,149,549 | A | 4/1979 | Grossman | |
| 4,178,438 | A | 12/1979 | Haase et al. | |
| 4,230,573 | A | 10/1980 | Kilty et al. | |
| 4,242,226 | A | 12/1980 | Siren | |
| 4,282,261 | A | 8/1981 | Greene | |
| 4,288,462 | A | 9/1981 | Hou et al. | |
| 4,305,782 | A | 12/1981 | Ostreicher et al. | |
| 4,309,247 | A | 1/1982 | Hou et al. | |
| 4,321,288 | A | 3/1982 | Ostreicher | |
| 4,331,631 | A | 5/1982 | Chapman et al. | |
| 4,366,068 | A | 12/1982 | Ostreicher et al. | |
| 4,395,332 | A | 7/1983 | Klein | |
| 4,433,697 | A | 2/1984 | Cline et al. | |
| 4,455,187 | A | 6/1984 | von Blucher et al. | |
| 4,473,474 | A | 9/1984 | Ostreicher et al. | |
| 4,510,193 | A | 4/1985 | Blucher et al. | |
| 4,511,473 | A * | 4/1985 | Hou | 210/348 |
| 4,523,995 | A | 6/1985 | Pall et al. | |
| 4,536,440 | A | 8/1985 | Berg | |
| 4,555,347 | A | 11/1985 | O'Dowd et al. | |
| 4,604,208 | A | 8/1986 | Chu et al. | |
| 4,606,823 | A | 8/1986 | Lucas, III | |
| 4,617,128 | A | 10/1986 | Ostreicher | |
| 4,664,683 | A | 5/1987 | Degen et al. | |
| 4,673,504 | A | 6/1987 | Ostreicher et al. | |
| 4,677,019 | A | 6/1987 | von Blucher | |
| 4,708,803 | A | 11/1987 | Ostreicher et al. | |
| 4,711,793 | A | 12/1987 | Ostreicher et al. | |
| 4,743,418 | A | 5/1988 | Barnes, Jr. et al. | |
| 4,761,323 | A | 8/1988 | Muehlratzer et al. | |
| 4,807,619 | A | 2/1989 | Dyrud et al. | |
| 4,824,451 | A | 4/1989 | Vogt et al. | |
| 5,085,784 | A | 2/1992 | Ostreicher | |
| 5,104,546 | A | 4/1992 | Filson et al. | |
| 5,109,311 | A | 4/1992 | Hanazono et al. | |
| 5,126,044 | A | 6/1992 | Magnusson et al. | |
| 5,147,722 | A | 9/1992 | Koslow | |
| 5,189,092 | A | 2/1993 | Koslow | |
| 5,219,577 | A | 6/1993 | Kossovsky et al. | |
| 5,225,078 | A | 7/1993 | Polasky et al. | |
| 5,307,796 | A | 5/1994 | Kronzer et al. | |
| 5,350,443 | A | 9/1994 | von Blucher et al. | |
| 5,366,636 | A | 11/1994 | Marchin et al. | |
| 5,486,292 | A | 1/1996 | Bair et al. | |
| 5,547,607 | A * | 8/1996 | Ando et al. | 516/94 |
| 5,562,824 | A | 10/1996 | Magnusson | |
| 5,744,236 | A | 4/1998 | Rohrbach et al. | |
| 5,759,394 | A | 6/1998 | Rohrbach et al. | |
| 5,798,220 | A | 8/1998 | Kossovsky et al. | |
| 5,804,295 | A | 9/1998 | Braun et al. | |
| 5,855,788 | A | 1/1999 | Everhart et al. | |
| 5,865,968 | A | 2/1999 | Denton et al. | |
| 6,010,606 | A | 1/2000 | Denton et al. | |
| 6,057,488 | A | 5/2000 | Koper et al. | |
| 6,077,588 | A | 6/2000 | Koslow et al. | |
| 6,197,515 | B1 | 3/2001 | Bamdad et al. | |
| 6,235,388 | B1 | 5/2001 | Yamamoto et al. | |
| 6,290,848 | B1 | 9/2001 | Tanner et al. | |
| 6,321,915 | B1 | 11/2001 | Wilson et al. | |
| 6,355,330 | B1 | 3/2002 | Koslow et al. | |
| 6,402,819 | B1 | 6/2002 | DeRuiter et al. | |
| 6,464,757 | B2 | 10/2002 | Zhang et al. | |
| 6,514,413 | B2 | 2/2003 | Pimenov et al. | |
| 6,524,477 | B1 | 2/2003 | Hughes | |
| 6,550,622 | B2 | 4/2003 | Koslow | |
| 6,565,749 | B1 * | 5/2003 | Hou et al. | 210/500.38 |
| 6,630,016 | B2 * | 10/2003 | Koslow | 95/285 |
| 6,716,218 | B2 | 4/2004 | Holmes et al. | |
| 6,716,525 | B1 | 4/2004 | Yadav et al. | |
| 6,797,167 | B2 | 9/2004 | Koslow | |
| 6,830,822 | B2 | 12/2004 | Yadav | |
| 6,838,005 | B2 * | 1/2005 | Tepper et al. | 210/660 |
| 6,849,109 | B2 | 2/2005 | Yadav et al. | |
| 6,872,311 | B2 | 3/2005 | Koslow | |
| 6,872,431 | B2 | 3/2005 | Kahlbaugh et al. | |
| 6,913,154 | B2 | 7/2005 | Koslow | |
| 6,953,604 | B2 | 10/2005 | Koslow | |
| 6,955,708 | B1 | 10/2005 | Julos et al. | |
| 6,959,820 | B2 | 11/2005 | Koslow | |
| 2003/0127393 | A1 | 7/2003 | Tepper | |
| 2005/0029198 | A1 | 2/2005 | Tepper et al. | |
| 2006/0123991 | A1 | 6/2006 | Braeunling et al. | |
| 2006/0163174 | A1 | 7/2006 | Namespera et al. | |
| 2006/0169144 | A1 | 8/2006 | Forslund | |
| 2006/0225574 | A1 | 10/2006 | Braeunling et al. | |

FOREIGN PATENT DOCUMENTS

| | | | |
|---|---|---|---|
| DE | 2510467 A | | 9/1976 |
| EP | 0099586 | | 2/1984 |
| EP | 0958851 A | | 11/1999 |
| EP | 1 219 335 A1 | | 7/2002 |
| GB | 2045828 A | | 11/1980 |
| RU | 2063383 | * | 7/1996 |
| RU | 2168357 | * | 6/2001 |
| SU | 1066942 | * | 1/1984 |
| WO | 98/02231 A1 | | 1/1998 |
| WO | WO 99/47456 | | 9/1999 |

OTHER PUBLICATIONS

Farrah, S.R. et al., (1991), Adsorption of viruses from water by using cellulose filters modified by in-situ precipitation of ferric and aluminum hydroxides, Applied Environmental Microbiology, 1502-1504 (abstract).

Mandaro, R., (1987), Charge modified depth filters: cationic-charge modified nylon membranes, Filtration in the Pharmaceutical Industry, T.H. Meltzer Ed., Marcel Dekker, Inc., New York, NY.

Meltzer, T.H. et al., (1998), Filtration in the biopharmaceutical industry, Marcel Dekker, New York, NY, pp. 262-265.

Sinha, D., (1990), Pretreatment process considerations for the semiconductor industry, Ultrapure Water 7(6): 21-30.

Willkommen, H., (Oct. 1-Oct. 3, 2001), Virus validation for filtration procedures, PDA/FDA Viral Clearance Forum, Bethesda, MD.

Yavorosvsky, N.A., (1996), Izvestiia VUZ, Fizika 4:114-35.

Yavorovsky, N.A. et al., (2000), Ultra-fine powder by wire explosion method, Acta Materialia 44(8/9): 2247-2251.

Tien, Chi, Adsorption Calculations and Modeling, 1994 Butterworth-Heinemann (TOC provided).

Blackford, D.B. et al., Alteration in the Performance of Electrostatic Filters Caused by Exposure to Aerosols, 4th World Filtration Congres, 7.27-7.33.

Wilkie, A.E. et al., Multi-Component Fiber Technology for Medical and Other Filtration Applications, 1st Inter. Conf. on Med. Filtration, DE Oct. 9, 2002.

Raynor, P.C. et al., The Long-Term Performance of Electrically Charged Filters in a Ventilation System, J. of Occ. and Envir. Hygiene, vol. 1(7): 463-471, Jul. 2004.

Martin, S.M. et al., Electrostatic Respirator Filter Media: Filter Efficiency and Most Penetrating Particle Size Effects, Appl. Occ. & Enviro. Hygiene vol. 15(8):609-17, 2000.

Moyer, E.S. et al., Electrostatic N-95 Respirator Filter Media Efficiency Degradation Resulting from Intermittent NaCl Aerosol Expos., Appl. Occ. & Envir. Hyg. 15(8): 600-8.

Brown, R.C. et al., Effect of Industrial Aerosols on the Performance of Electrically Charged Filter Material, Hyg. vol. 32(3): 271-94, 1988.

Henderson, D.W. et al., An Apparatus for the Study of Airborne Infection, J. Hyg. Camb. vol. 50, p. 53-67, 1952.

Johnson, P.R., Whadaya Mean?, Filtration News VOl 20(5): 10-11, 2002.

Ahuja, S., Handbook of Bioseparations, Academic Press, 2000, TOC.

Farrah, S.R. et al., Concentration of Viruses from Water by Using Cellulose Filters Modifies by In-situ Precipitation of Ferric and Aluminum Hydroxides, Appl Envir Micro, 1985.

Gitzen, W.H., Alumina as a Ceramic Material, American Ceramic Soc., Special Pub. 4, 1970, 13-14, TOC.

Hou, K. et al., Capture of Latex Beads, Bacteria, Endotoxin and Viruses by Charge-Modified Filters, Appl Envir Micro, Nov. 1980, 892-96.

Khalil, K., Synthesis of Short Fibrous Boehmite Suitable for Thermally Stabilized Transition Aluminas Formation, Journal of Catalysis, 1198 (178):198-206, Abstract.

Lukasik, J. et al., Influence of Salts on Virus Adsorption to Microporous Filters, Appl Environ Micro, 66: 2914-20.

Lukasik, J. et al., Removal of Microorganisms from Water by Columns Containing Sand Coated with Ferric and Aluminum Hydroxides, Wat Res 33(3): 769-77, 1999, Abstract.

Sobsey, M.D. et al., Concentration of Poliovisur from Tap Water Using Positively Charged Microporous Filters, Appl Enviro Micro, 1979: 588-595.

Tepper, F., Nanosize Powders Produced by Electro-Explosion of Wire and Their Potential Applications, Argonide Corporation, Sanford, FL, Abstract.

Robinson et al., Depyrogenation by Microporous Membrane Filters, Tech Rpt No. 7, Depyrogenation, Parenteral Drug Assn, Phila, PA, 1985, TOC.

* cited by examiner

SUB-MICRON FILTER

CROSS-REFERENCE TO A RELATED APPLICATION

This Application is a continuation-in-part of application Ser. No. 10/177,709, filed Jun. 21, 2002, now U.S. Pat. No. 6,838,055, which claims the benefit of U.S. Provisional Application Ser. No. 60/300,184, filed Jun. 22, 2001.

STATEMENT OF GOVERNMENTAL RIGHTS

The subject invention was made with support under a research project supported by the U.S. Department of Energy Cooperative Research and Development (CRADA) Agreement No. 99-USIC-MULTILAB-04 and LOS ALAMOS NATIONAL LABORATORY CRADA No. LA99CI0429. Accordingly, the government has certain rights in this invention.

FIELD OF THE INVENTION

The subject invention pertains to the field of nano fibers, more particularly to the use of nano fibers as filter media and in bio separation processes.

BACKGROUND OF THE INVENTION

Waterborne pathogenic microorganisms are a major source of disease worldwide. Despite measures instituted to ensure the microbiological safety of drinking water, disease-causing microorganisms are regularly transmitted via water supplies. The principal waterborne bacteria of concern are *Salmonella* spp., *Shigella* spp., *Yersinia* spp., *Mycobacterium* spp., *enterocolitica*, as well as *Escherichia coli, Campylobacter jejuni, Legionella, Vibrio cholerae*. These bacteria range from 0.5 to several microns and are either ovoid (cocci) or rod-like (bacillus) in shape. Cryptosporidium and other protozoa are about 3-5 microns in size and are resistant to many forms of chemical disinfection. *Cryptosporidium* has been responsible for several major pollution events and many deaths.

The EPA Science Advisory Board ranks viruses in drinking water as one of the highest health risks. Waterborne pathogenic viruses include Enteroviruses, (such as polioviruses, Coxsackievirus (groups A and B), echoviruses, hepatitis A virus), rotaviruses and other reoviruses (Reoviridae), adenoviruses, and Norwalk-type agents. The numbers of viruses detected per liter of sewage range from less than 100 infective units to more than 100,000 infective units. In some instances, the ingestion of a single infectious unit can lead to infection in a certain proportion of susceptible humans. Constant exposure of large population groups to even relatively small numbers of enteric viruses in large volumes of water can lead to an endemic state of virus dissemination in the community. Currently, there are no EPA regulations mandating virus removal, due to the fact that the hazard has not been adequately quantified. There are, however, military specifications requiring the removal of viruses (as Hepatitis)>4 logs (>99.99%) as well as bacteria (as *E. coli*)>5 log (99.999%) and Cryptosporidium>3 logs (99.9%).

The principal disinfection methods are chemical oxidation and micro filtration. Chemical oxidants include ozone, chlorine and chlorine derivatives. Viruses are more resistant to environmental conditions and sewage treatment processes, including chlorination and UV radiation, than many of the sewage-associated bacteria. In laboratory studies, enteric viruses survive for up to 130 days in seawater, surpassing those reported for coliform bacteria.

There is growing concern about the toxicity and potential carcinogenicity of disinfectant by-products (DBP's) that form as a result of chemical treatment. In public water supplies, it has not been cost effective to substitute filter sterilization because the flow rate of filters rated for virus removal is far too low to be practical. Further, because pathogenic bacteria can proliferate in piping, filtration at the point of use is preferable. Point of entry (POE) and point of use (POU) purification systems based on reverse osmosis (RO) filtration or ultraviolet treatment (UV) are generally used for removing microbial pathogens from municipal water as well as from untreated ground water sources. Both RO and UV systems are limited by low flow rates and require water reservoirs to sustain effective flow when taps are open. In addition, complete sanitization by UV is uncertain because pathogens may be shielded by colloidal particles. Thus, filtration is a necessary adjunct. Both RO and UV systems tend to be rather expensive for a small POU (single faucet) system and are very complex, requiring extensive service for maintenance. A filter capable of removing all microbial pathogens is of great value. Further, it is a major economic advantage to produce a filter that can be installed with as much as ease as installing current chemical filters.

Purifying water is also important in medical and dental offices. Dental-unit water systems (DUWS) harbor bacterial biofilms that serve as a haven for pathogens that often exceed dental association standards. The pathogens found include many serious species such as *Legionella pneumophila* and contamination of water lines with viruses and potentially HIV or Hepatitis virus could occur from back siphoning of fluids from prior patients. A POU filter capable of sanitizing DUWS water by removing bacteria and virus at high flow rate is also desired for dental suites.

Colloidal contamination of water can contribute to turbidity (cloudy appearance) of water. Such colloidal particles generally include organic matter such as humic material, pathogens, as well as nano size inorganic minerals. Colloids provide sorption sites for microbes, pesticides, other synthetic organic chemicals, and heavy metals. Their nano size dimensions tend to clog filter systems.

Improved technology is needed in the detection and identification of pathogens and particularly viruses because methods of concentrating them are not efficient. Low cost samplers of virus are needed for assaying surface waters. While such filters need not be sterilization grade, the collector should be capable of removing the bulk of virus from a 500-1000 liter water sample within two hours. Then the virus on the filter must be eluted intact and viable for subsequent analysis. AMF Cuno's MDS-1 filter is predominant in the analysis of environmental water for virus. Unfortunately such filters are cost prohibitive for routine use, particularly since these are single use filters. The price for single use filters must be significantly reduced before the EPA would consider virus sampling as a routine procedure. Recently, potential terrorist use of biological weapons (BW) in air and water has increased the need for early detection and measurement. Effective detection is difficult due to the limited sensitivity of current bio-analytical methods, particularly with virus that are much smaller, more difficult to concentrate and more likely to be pathogenic. Tens to hundreds of liters of air or water need to be sampled to provide sufficient particles for detection in a sample. Particle collectors for air sampling are limited to cyclone separation and impactors and are impractical for virus size particles.

Fibrous depth filters retain particles principally by impaction of the particle onto the fiber where they adsorptively adhere while membranes retain particles principally by size exclusion. Membranes are available with pore sizes small enough to sieve out bacteria and viruses, but fibrous depth filters are incapable of sanitizing water. In the context of filtration separations, pore sizes in reverse osmosis membranes extend from about 1 to 10 Å to 20 Å, ultra filtration from about 1 nanometer (10 Å) to 200 nm, micro filtration from about 50 nm or 0.05 micron to about 2 microns, and particle filtration from about 1 to 2 microns and up. As the size of the pathogen decreases, the pore size of the filtration membrane must be reduced. This results in a drastic pressure drop and reduces process flow rates. Many viruses are as small as 30 nm and commercially available membranes are limited to approximately 2 to 3 log reduction for such small particles [Willcommen]. Membranes are susceptible to clogging, and pre-filters must be used to remove coarser particles to extend the life of the more expensive membrane. Furthermore, membranes are susceptible to point defects such as overlapping pores and finger voids that greatly affect reliability.

Virus must be removed from proprietary medicinal products as well as human blood and plasma-derived products. FDA has recommended that all purification schemes use one or more 'robust' virus removal or inactivation steps. Robust steps were defined as those that work under a variety of conditions and include low pH, heat, solvent-detergent inactivation and filtration. Virus removal via heat, chemical, ultraviolet or gamma radiation could denature sensitive proteins and further require the removal of said chemical agents or denatured proteins. Accordingly, filtration is regarded as a preferred method of virus removal.

In recent years there has been a remarkable expansion of biotechnology including the synthesis of proteins formed via recombinant methods, removal of proteins from blood plasma, modified hemoglobin products, mammalian serum products as well as protecting fermenters from contamination by viruses. Prions are proteins suspected of causing Creutzfeldt-Jacob disease (CJC). They are about 10 mm in size, thus, smaller than virus. In pharmaceutical manufacture, micro porous and ultra porous membranes are used to purify incoming process water streams as well as control effluents and by-product streams to assure that there is no contamination of water discharges.

Originally 0.45 micron filters were regarded as "sterilization rated" based on their ability to efficiently retain *Serratia marcescens* organisms, but studies showed that the filter could be compromised. A smaller bacteria *Pseudomonus diminuta* (*P. diminuta*) (0.3μ) is now widely used for testing filter integrity, and a 0.22μ pore filter is now accepted as sterilization grade in removing bacteria. Ultra porous membranes, with pore sizes as small as 20 nm are used for filtering virus. Nano porous membranes such as used in reverse osmosis are capable of filtering virus, but with even further increases in flow restriction. In the manufacture of proteins, regulatory authorities suggest that sterilization from viruses should require a virus reduction factor (LRV) of at least 12 orders of magnitude. This value is calculated to result in less than one infectious particle per $10^6$ doses. Such a level of virus removal currently requires multiple step processes.

Packed beds containing multivalent cations such as Al3+ and Mg2+ at a pH of about 3.5 may retain viruses. Lukasik et al. were able to remove viruses efficiently from raw sewage laden water over significant time using deep beds of sand modified with ferric and aluminum hydroxides. Farrah incorporated metallic oxides of aluminum and other metals into diatomaceous earth and achieved significant improvement in adsorption of viruses. Farrah and Preston improved the adsorption of several viruses by modification of cellulose fiber filters with flocculated ferric and aluminum hydroxides.

Filters may be constructed from a wide variety of materials. While glass fiber filters tend to be weak, a number of chemical binders will improve their physical properties and modify their chemical characteristics. Ceramic filters often have desirable combinations of properties, but they can be brittle. Metal filters often overcome this limitation, but they can be expensive. The benefit to using ceramic and metal filters is that they are often cleanable and reusable. Filter fibers or membranes are produced from a variety of polymers including: polyvinylidene difluoride (PVDF), polyolefin and acrylics. Sorbents such as granular silica, diatomaceous earth or granular carbon have also been incorporated into filter media.

Electro kinetic forces aid the capture of particles from water. Hou has described a qualitative picture of filtration by electro kinetic phenomena, where the phenomenon is explained by concepts similar to those in colloidal chemistry. If the electrostatic charges of the filter media and particulates are opposite, electrostatic attraction will facilitate the deposition and retention of the particles on the surface of the filter media. If they are of similar charge, repulsion will occur and deposition and retention will be hindered. The surface charge of the filter is altered by changes in pH and the electrolyte concentration of the solution being filtered. This phenomenon is explained by the electric double-layer theory of colloidal chemistry. A particle immersed in an aqueous solution develops a surface charge by adsorbing ions on its surface. A fixed layer of oppositely charged ions develops around the surface of the filter. To maintain the electrically neutral system, there is a diffused layer containing a sufficient number of counter-ions extended for some distance into the solution. If the bulk solution of counter-ions increases by addition of cationic salts or increasing pH, the thickness of this layer decreases because less volume is required to contain enough counter-ions to neutralize the surface charge. The reduction of thickness of this layer facilitates the approach of the two surfaces, allowing Van der Waals forces to take effect. Lowering the pH or adding cationic salts thus reduces electronegativity, and allows for some adsorption to occur under these conditions. Virus adsorbance is facilitated in most natural and tap water, having pH ranging between about 5-9 [Sobsey]. Acid or salt addition is often needed to effect virus removal by electronegative filters. Hou claims that electropositive filters have widespread application in the removal of microorganisms from water, for the concentration of both bacteria and viruses from water and harvesting for removal of endotoxins from contaminated partenterals and foods, and for immobilization of microbial cells and antigens.

Fibrillated asbestos, having an electropositive surface charge and a surface area of approximately 50 m$^2$/g was used extensively as cellulose/asbestos filter sheets for filtering pathogens. The fibers of asbestos produced a very fine pore structure that was capable of mechanical straining as well. However, concerns about the health hazards of asbestos terminated its use, and efforts began to develop an asbestos substitute. These efforts included attempts to chemically modify the surfaces of hydrophobic polymeric filter materials to produce coatings with electropositive charges.

For example, U.S. Pat. Nos. 4,007,113; 4,007,114; 4,321, 288 and 4,617,128 to Ostreicher, describe the use of a melamine formaldehyde cationic colloid to charge modify fibrous and particulate filter elements. U.S. Pat. Nos. 4,305, 782 and 4,366,068 to Ostreicher, et al. describe the use of an inorganic cationic colloidal silica to charge modify such elements. In U.S. Pat. No. 4,366,068, the "fine" silica particle exhibits an average particulate dimension of less than about 10 microns and is coated with at least 15% alumina. U.S. Pat. No. 4,230,573 to Kilty, et al. describes the use of polyamine epichlorohydrin to charge modify fibrous filter elements, see also U.S. Pat. No. 4,288,462 to Hou, et al., and U.S. Pat. No. 4,282,261 to Greene. Preferred methods of making filter media are described in U.S. Pat. No. 4,309,247 to Hou, et al. and are being sold by Cuno, Inc. under the trademark ZETA PLUS. Similar attempts at cationic charging of filters were made in U.S. Pat. Nos. 3,242,073 and 3,352,424 to Guebert, et al., and U.S. Pat. No. 4,178,438 to Hasse, et al. U.S. Pat. No. 5,855,788 to Everhart describes a method of modifying the surface of filters based on woven or non-woven fabrics, or aperture polymers by adsorbing amphiphilic protein such as derived from milk. The protein is modified with metal hydroxides such as alumina derived from sol-gel reactions. The filters remove waterborne pathogens primarily by chemical and electrokinetic interactions rather than by sieving. A log 3 reduction was obtained for *Vibrio cholerae* bacteria. The inventors observed that filters having modified surface charge characteristics have different filtration efficiencies for different types of waterborne pathogens, such as, for example, different types of bacteria.

U.S. Pat. No. 5,085,784 to Ostreicher proposes a charge modified filter media comprising cellulose fiber, silica based particulate, and a cationic water-soluble organic polymer. The polymer is adsorbed onto the filter that includes an epoxide and a quaternary ammonium group, capable of bonding to a secondary charge-modifying agent. The modifying agent is preferably an aliphatic polyamine. U.S. Pat. No. 4,523,995 to Pall describes a filter media prepared by mixing glass, with polyamine-epichlorohydrin resin, to form a dispersion. A precipitating agent is added to the dispersion to precipitate the resin and coat the microfibers. The preferred precipitating agents are high molecular weight polymers containing anionic charges. The resulting coated microfibers are described as having a positive zeta potential in alkaline media and enhanced particulate removal efficiencies for fine particulate removal, including bacteria and endotoxins (pyrogens). However, Robinson et al., Mandaro and Meltzer describe the limitations of prior art cationic charge modified media in terms of general loss of filtration performance at high pH and, the inability of such media to achieve effective removal of very fine particle and/or pyrogens (endotoxins) removal.

Cationically charged membranes, used for the filtration of anionic particulate contaminants, are also known and described in U.S. Pat. No. 2,783,894 to Lovell and U.S. Pat. No. 3,408,315 to Paine. U.S. Pat. Nos. 4,473,475 and 4,743,418 to Barnes, et al. describes a cationic charge-modified micro porous nylon membrane having a charge-modifying amount of an aliphatic amine or polyamine, preferably tetra-ethylene pentamine bonded to the nylon. U.S. Pat. No. 4,604,208 to Chu, et al. describes an anionic charge modified nylon micro porous filter membrane. The charge-modifying system is a water-soluble polymer capable of bonding to the membrane and anionic functional groups such as carboxyl, phosphorous, phosphonic, and sulfonic groups. U.S. Pat. Nos. 4,473,474; 4,673,504; 4,708,803 and 4,711,793 to Ostreicher, et al., describe a nylon membrane charge modified with epichlorohydrin-modified polyamide having tertiary amine or quaternary ammonium groups, and a secondary charge-modifying agent that may be an aliphatic polyamine. Cationic charge modified nylon membranes covered by these patents to Ostreicher, et al. and Barnes, et al. are now being sold by Cuno, Inc., under the trademark ZETAPOR. Positively charged modified microporous filter media are available from Pall Corp., that uses nylon 66 or a positively charged polyethersulfone sulfate membrane. Micropore Corp. produces a charge-modified poly vinylidene difluoride (PVDF) membrane.

Filters are used generally in two different modes. In the depth or dead end filter, all the fluid flows through the membrane or media. In the cross-flow (tangential) flow filter the feed flow is axially channeled, while pure liquid (permeate) flow through the filter media. This type of filter limits the thickness of the filter cake making and allowing greater flowrate, while in conventional dead-end filtration, the filter cake increases with time, resulting in pressure drops that cause cessation of flow. Filtration speed is important in virtually all industrial processes including pharmaceutical manufacturing, biological processing, and laboratory experimentation. Membranes used in filtering sub-micron to nanometer size particles have very low flux unless compensated for by substantial increases in pressure on the filter or by increases in filter membrane area. Increasing pressure or filter area markedly increases capital and operating costs. Clogging further degrades the low flux of small pore membranes.

Pyrogens are substances that contain endotoxins that are fever-inducing substances. Endotoxins are high molecular weight (between 10,000 to 1 million) complexes, which derive from gram-negative bacteria that shed their outer membrane into the environment, causing fever in humans. The endotoxin is not affected by autoclaving because it is stable for several hours at 250° C. Endotoxins can, however, be removed by reverse osmosis but RO processing is difficult because of the small membrane pore size. Moreover, desirable substances such as salts are excluded by reverse osmosis and this is a drawback in forming non-pyrogenic parenteral solutions. U.S. Pat. No. 5,104,546 describes a ceramic ultra-filter that is capable of separating pyrogens from parenteral fluids. The ceramic ultra-filter is a zirconium oxide layer over an alumina ceramic having a nominal pore size of about 5 namometers. The filter is capable of separating pyrogens to the extent of 5 logs, however significant driving pressure (80 psi) and a cross-filter length of 20 cm are required to produce an initial flux of only 50 L/hr/m$^2$/atmosphere.

New analytical schemes are being developed for pharmacological or biochemical materials, where specific reagents are retained onto high surface area substrates. Membranes are also commonly used as supports for diagnostic assays like electrophoresis, cytology of fluids, and DNA hybridization. Many analytical methods involve immobilization of a biological binding partner of a biological molecule on a surface. The surface is exposed to a medium suspected of containing the molecule, and the existence or extent of molecule coupling to the surface-immobilized binding partner is determined. For instance, in U.S. Pat. No. 5,798,220 a native macromolecule is bound to a support surface and used in an immunoassay to screen biological fluids for antibodies to the macromolecule in its bound state. U.S. Pat. No. 5,219,577 describes a synthetic biologically active composition having a nanocrystalline core. U.S. Pat. No. 6,197,515 describes for a method of capturing a biological molecule, for example at a biosensor surface, by exploiting biological binding interactions. A substrate that would efficiently bond the first biological molecule would facilitate such analytical strategies. Nucleic acids are sorbed to metal oxide supports including alumina to enable the resulting compositions to be used for hybridizing, labeling, sequencing, and synthesis.

Electrophoresis is one of the most widely used separation techniques in the biologically related sciences. Molecular species such as peptides, proteins, and oligonucleotides are separated as a result of migration in a buffer solution under the influence of an electric field. This buffer solution normally is used in conjunction with a low to moderate concentration of an appropriate gelling agent such as agarose or polyacrylamide to minimize the occurrence of convective mixing. The highest resolution is obtained when an element of discontinuity is introduced in the liquid phase. Elements such as pH gradients, or the sieving effect of high-density gels have a great influence on the separation of different size molecules. Membrane barriers may also be introduced into the path of migrating particles. High surface area electropositive absorbers, if added to such gels, can enhance separation factors.

The "Genetic Revolution" is creating a need for technologies related to bio-separation. Because recombinant retrovirus, sadenovirus of adeno-associated virus vectors offer some of the best vehicles for accomplishing efficient transfer and integration of genetic material, there is a clear need for virus isolation methods which are both effective and cause little or no damage to the viral particles. Density gradient centrifugation has always played an important part in concentration and purification of virus particles but the gradient media used most prominently, for example, sucrose and CsCl, pose a number of problems. Both media are highly hyperosmotic and the entities used to bond viruses generally have to be removed by ultra filtration prior to further processing or analysis. Moreover, a precipitating agent that would remove virus by precipitation, or efficient low-pressure drop filtration, would facilitate such processing. [Nycomed]

Separation of macromolecules such as proteins is a considerable cost in the manufacture of pharmacological products. Chromatography has been used for decades to perform biological separations. In chromatography, a mixture is applied in a narrow initial zone to a stationary sorbent and the components are caused to undergo differential migration by the flow of the liquid. In the case of ion chromatography, that differential migration is caused by the divergent attraction of charged molecules in an oppositely charged stationary phase. Chemically modified cellulose containing silica is used for the stationary phase in the manufacture of commercially important biomolecules in the food, biopharmaceutical, biotechnology and pharmaceutical industries. For example, such media used in many different large-scale processes for the manufacture of antibodies, enzymes, peptides, plasmids and hormones. Alternative stationary phases can include metals and metal oxides, for example, particulate aluminum oxide. Membrane absorbers (MA) are membranes with functionalized surface sites for chromatography. The resolution of traditional chromatography beads is inversely proportional to the size of the beads and MA devices produce very high resolution because they have higher external surface area compared to granules. A fibrous media capable of such resolution having lower flow restrictions would provide even more rapid and economical separation, for both purifying solutes and for analytical purposes.

Fine aluminum hydroxide gels and sols have been used as precipitation aids and as powdered sorbents for organic macromolecules. For example, $Al(OH)_3$ is used bind vitamin K factors. Nucleic acids are often contaminants in solutions of protein and can be precipitated by exposure to nucleases, [Ahuja, p. 368] shear, low ionic strength or high pH. Most of these methods affect resident proteins and have a relatively low degree of selectivity. Because nucleic acids possess negatively charged phosphate residues, precipitating agents with positively charged groups have the ability to selectively remove of nucleic acids from solution. This principle has given rise to the search for several precipitating agents for nucleic acids.

Cells are often cultured in reactors to produce biological and pharmacological products. Such cells can be bacterial or mammalian. In order to maintain a cell culture, oxygen and other nutrients generally must be supplied to the cells. Cell cultures are usually maintained in reactors by perfusion, wherein a cell culture medium, including oxygen and other nutrients, is directed through the cell-culture reactor. Cell-culture reactors, however, can support only small cell loadings per unit of reactor volume. They can only operate within a small window of flow or agitation rates. Porous substrates that would immobilize cells while allowing greater nutrient and dissolved gas exchange, would allow greater reactor loading. Similarly, biocatalytic reactions are performed in reactors, where an enzyme catalyst is retained to a porous inorganic support. Immobilization enhances the enzymes thermal and chemical robustness, while maintaining a high catalytic activity over a wide range of environmental conditions. A high surface area electropositive support would retain and immobilizes enzymes, providing for more rapid chemical reaction.

Ultra-pore water is used in a number of industries. Membrane ultra-filters are used to produce high purity water for the fabrication of microelectronics. Spiral wound membranes, another commonly employed technology, are readily affected by particles in the stream that restricts liquid flow paths through their extremely narrow channels. The fouling of polymeric ultra-filters is a major drawback as is the requirement to periodically clean these filters off line. [Sinha].

BRIEF SUMMARY OF THE INVENTION

The invention involves uses of a nano size form of alumina fiber or platelet that has been found to be highly electropositive, bio-adhesive in water. We have discovered that these fibers attract and retain colloidal and in particular virus particles and are very efficient precipitation aids. When incorporated into a fiber-based matrix, they are capable of filtering bacterial and particularly sub-micron particulates such as viruses or colloids with efficiency far greater than that of commercially available filters, especially in neutral water. Virus and nano size particles are retained at flow rates tens to hundreds of times greater than ultra porous membranes having pores capable of equivalent removal. Such nano alumina fiber filters have greater resistance to clogging by ultra fine particles. The filter media may be employed in filter sterilization of drinking water and medical or pharmaceutical process streams. By displacing the adsorbed particles, the filters can be used as a pre-concentrator for the purposes of detection and measurement of adsorbed pathogens. Such filters are very efficient separators in "membrane" chromatography for purification and analysis. The fibrous sorbent either in the form of a packet bed or as filter media can also be used to separate particles and macromolecules based upon their charge. Such fibers or filters derived from them would be improved substrates/media in bioreactors.

Accordingly, it is an object of the present invention to provide an electropositive sorbent and methods of making and using same.

Further objects and advantages of the present invention will become apparent by reference to the following detailed disclosure of the invention and appended figures.

DETAILED DISCLOSURE OF THE INVENTION

Figure 1:
FIG. 1 is a transmission electron microscope (TEM) of nano fibers produced by hydrolysis of nano aluminum prepared in argon. 2 nanometer diameter fibers are in focus-center foreground.

In order to provide an understanding of a number of terms used in the specification and claims herein, the following definitions are provided.

The term electronegative particle as used herein is defined as an entity that has an electronegative surface charge, not including atoms in ionic form, but including such entities as viruses, bacteria, pyrogens, prions, macromolecules, nucleic acids, colloids, proteins and enzymes.

The term desorption as used herein refers to the process of removing an adsorbed electronegative particle from the surface of an eletropositive sorbent.

The term nano alumina, as used herein, is defined as particles with a longitudinal/cross section ratio in excess of about 5, where the smallest dimension is less than about 100 nanometers. The cross section of the "fiber" may be circular (cylindrical fiber) or rectangular in shape (platelet). The fibers are comprised of alumina, with various contents of combined water to result in compositions of pure $Al(OH)_3$ or AlOOH or mixtures of the two, with possible impurities of gamma and alpha alumina.

The term, NanoCeram™ as used herein, is defined as nano alumina as described above.

The term sol as used herein is defined as a fluid colloidal system.

Nano size aluminum hydroxide fibers may be produced by a number of different methods. U.S. Pat. Nos. 2,915,475 and 3,031,417 describe the preparation of boehmite fibers from very low cost chemicals (alum, sodium bicarbonate and acetic acid) by a hydrothermal reaction. Gitzen describes several methods of producing fibers, including reacting aluminum amalgams with water and by reacting aluminum with acetic acid. After aging of the sol produced by this latter reaction, fibrous hydrated alumina crystals 20 nm-50 nm in diameter are formed. Alumina fibers have also been produced by the controlled oxidation of molten aluminum by a mixture of oxygen and a gas diluent. However, small globules of aluminum usually contaminate the fibers. U.S. Pat. No. 3,947,562 describes its preparation via the oxidation of gaseous aluminum trichloride with carbon dioxide at 1275° C.-1700° C. in the presence of sufficient hydrogen to combine with the chlorine to form HCl. These fibers are very coarse and have particles as well as other forms present. U.S. Pat. No. 4,331,631 describes the formation of alumina fibers by oxidizing stainless steel containing aluminum. The alumina fiber coating was adherent and used for fabricating automotive catalytic converters after impregnating the alumina-base coating with platinum. Khalil produced long and short boehmite fibers by hydrolysis of aluminum alkoxide.

The preferred aluminum oxide fibers produced in the instant invention is by the reaction of micron size and preferably nano size aluminum powder with water. The electro explosion of metal wire preferably produces the preferred aluminum metal powder. Aluminum wire with a diameter of about 0.3 mm is fed into a reactor containing about 3 atmospheres of argon absolute. A section about 100 mm long is electrically exploded by applying to the wire about 500 Joules (about 25 KV@peak voltage of 20 KA where the capacitance of the capacitor bank is 2.4 μF). During the pulse that lasts about 1 microsecond, temperatures exceeding 10,000 Kelvin are produced, as well as x-ray and ultraviolet energy. Metal clusters are propelled through the argon resulting in high quench rates and a complex microstructure in the aluminum once frozen. Yavorovski describes the process and equipment. The aluminum may be exposed to dry air to passivate (oxidize) the surface so that it can be handled in ambient air without ignition. The resulting nano aluminum spheres are fully dense spherical particles with an average size of about 110 nanometers and are somewhat agglomerated. The BET surface area is approximately 20 $m^2$/g.

The resulting nano metal aluminum is reacted with water at 75° C. to produce alumina sol that is filtered and subsequently heated. In the first step, the powder is dried at 100° C.-110° C. The resulting powders are heat-treated at a temperature range of about 200° C.-450° C. creating a mixture of aluminum hydroxide, $Al(OH)_3$ and boehmite (AlOOH). The higher the temperature, the greater the boehmite yield and the lower the tri-hydroxide yield.

An alternate method involves electro exploding aluminum wire in a nitrogen environment, at 3 atmospheres absolute pressure. Nitrogen is lower cost than argon and eliminates the passivation step since the nitride coated nano aluminum is not pyrophoric. In this case, the aluminum metal particle is coated with a layer of aluminum nitride (AlN). When hydrolyzed, boehmite fibers are produced. Ammonia and hydrogen are also produced as the principal gaseous by-products.

Figure 2:
FIG. 2 is a TEM micrograph of nano fibers produced by hydrolysis of nano aluminum prepared in nitrogen.

Referring now to FIGS. 1 and 2, transmission electron microscope (TEM) micrographs show fibers that are about 2-3 nm in diameter. FIG. 1 shows fibers produced by hydrolysis of nano aluminum that had been prepared in argon gas and oxidized by exposure to dry air. The nano alumina fibers of FIG. 2 were prepared from nano aluminum powder that had been produced in a nitrogen environment, having an AlN coating. The fibers are somewhat aggregated in an open network with aspect ratios (length to diameter) up to 100 or more. The opaque regions are the result of non-dispersion and stacking of the fibers in the field of view. The BET surface area of the fibers in FIGS. 1 and 2 is approximately 475 $m^2$/g. The calculated surface area, assuming a 2 nm diameter would be approximately that observed in BET, indicating that most, if not all, of the surface area (at least available to nitrogen absorption) is on the external surface of the fiber. When reduced to the same TEM magnification, the nano fibers produced from either oxide or nitrogen-passivated forms of nano aluminum appear identical and have similar crystallographic patterns. All examples used nano aluminum prepared with argon, unless specifically designated otherwise.

Chemical and Structural Characterization of the Fibers— Weight loss on heating is 5.4% to 200° C., 6.7% more to 550° C. and 2.7% on calcining to 1100° C., for a total of 14% chemically combined water. The DTA curve is consistent with commercial boehmite, alpha alumina monohydrate; $\alpha\text{-}Al_2O_3.H_2O$ that has 15 wt % water. X-ray diffraction results showed that the sample, when heat treated at or below 300° C. is principally aluminum hydroxide, Al(OH)$_3$, and boehmite (AlOOH) with trace amounts of gamma phase alumina (Al$_2$O$_3$). After baking at about 465° C. for 3 hours, then at about 200° C. for 24 hours, the hydroxide and boehmite peaks disappeared. X-ray energy dispersive (XED) and Fourier Transform Infrared Spectroscopy (FTIR) spectra further confirm aluminas (including oxide-hydroxide components) as the major components.

Following are examples that illustrate procedures for practicing the invention. These examples should not be construed as limiting. All percentages are by weight and all solvent mixture proportions are by volume unless otherwise noted.

EXAMPLE 1

Table 1 presents absorption data of viruses by loose nano alumina fibers (0.7 g), prepared as described above. The nano fibers were supported by a series pair of 25 mm conventional micro porous filters (Millipore HA, 0.45 micron porosity) and tested against controls using Millipore HA filters only. The two filters were used in series to minimize the likelihood of by-pass in the first filter, due to the loose nature of the fibers. The two viruses, MS-2 and ϕX174, bacteriophages about 30 nm in diameter and spherical in shape were used. They were detected as plaque-forming units (PFU) using a double-layer assay with *Escherichia coli* C-3000 as the host. The test was performed at pH 7.5, which is well known to be unfavorable for virus electroadsorption by membranes. The test was performed where the influent flowed through the filters under equal rates for both the control and the test filter.

TABLE 1

Adsorption of Viruses by Nano Alumina Fibers

| Filter | Virus | % Virus Absorbed |
|---|---|---|
| Control | MS2 | <1% |
| | ϕX174 | <1% |
| nano alumina fiber | MS2 | 99.6% |
| | ϕX174 | 99.9% |

The results indicate very high retention of viruses as a result of adding the alumina fibers over the surface of the membrane control. Without being bound by any proposed theory, the following mechanism is proposed. The nano alumina fibers are alone hydrophilic. The surface area available externally on the fiber is about 5-10 times greater than that of fibrillated asbestos. The surface contains a high concentration of hydroxy groups attached thereto. The main components of the fiber are either aluminum hydroxide, $Al(OH)_3$, or boehmite (AlOOH) or a mixture of the two. The increased concentration of hydroxy groups results in a high electropositive charge on the fiber. The fibrous shape permits adequate spacing of positive charges as compared to the charge that would be accumulated should the particles be spherical.

The high electropositive charge attracts and retains electronegative particles or macromolecules. Should the bacteria not be excluded by the size of the pores between the agglomerated nano alumina particles, they would be captured by electrostatic adsorption. Bacteria are electronegative due to their cell wall chemistry. Gram-positive bacteria contain teichoic acid, a phosphate-containing polymer that produces a negatively charged surface. Gram-negative bacteria, abundant in water systems contain negatively charged —$COO^-$ groups associated with proteins and lipopolysaccharides in their cell walls. Other electronegatively charged entities include Gram-negative bacterial endotoxins (pyrogens) as well as viruses are negatively charged, as are inorganic and organic colloidal particles. In addition to high charge density, the large exposed surface area increases the speed of adsorption/adhesion resulting in thinner bed layers necessary if used in a dead-end (flow-through) mode. This also equates to shorter exchange paths when used in a cross-flow manner.

EXAMPLE 2

Bacteriophage MS-2 was diluted in 150 mL of 0.02 M imidazole/0.02 M glycine buffer (pH 7.2) to give an effective concentration of approx. $8\times10^5$/ml. Nano alumina fibers (0.5 grams) were placed into a 15 mL conical centrifuge tube containing 10 mL of the bacteriophage solution. The powder was completely dispersed by vortex mixing and was shaken on a rocking table for 15 minutes. The mixture was centrifuged at low speed (2500 rpm) to collect the powder at the bottom of the tube and the supernatant was assayed for the presence of virus. An initial and final aliquot was taken from the buffer solution containing bacteriophage, verifying the virus concentration remained constant throughout the time of the experiment. Table 2 indicates that process treatment temperatures between 150° C. and 450° C. had no noticeable affect on the attachment of either virus. The data also indicate that nano alumina fiber is a highly efficient precipitating agent, removing virus from solutions to >3.9 logs in one cycle.

TABLE 2

Adsorption of Virus from Water for Various Nano Alumina Fibers

| | $Log_{10}$ Reduction (MS-2) | |
|---|---|---|
| Treatment Temperature (° C.) | Sample N1 | Sample N2 |
| 150 | >3.9 | >3.9 |
| 200 | >3.9 | >3.9 |
| 250 | >3.9 | >3.9 |
| 300 | >3.9 | >3.9 |
| 350 | >3.9 | >3.9 |
| 400 | >3.9 | NA |
| 450 | >3.9 | >3.9 |

A device consisting of nano alumina fibers retained within a screened container or in the form of a fibrous mat would gather virus and other electronegative particles in a static system. If placed in a storage container containing water previously sterilized, the instant invention would collect bacteria and viruses, circulated by natural or forced convection and maintain sterility in the event of contamination, thus creating a microbial trap. The device, therefore, replaces the need for chemical disinfectant agents such as chlorine producing tablets, currently used, for instance, by the military, to maintain sterility. The microbial trap would provide better tasting water and reduce concerns about the negative health affects of disinfectant by-products (DBP's).

EXAMPLE 3

In order to avoid by-pass and channeling of fluids through packed beds of fibers, fibers are preferably integrated into a fibrous composite. Non-woven webs of fibers, 25 mm in diameter (surface area ~5 $cm^2$) were prepared by mulching a mixture of nano alumina with glass microfibers (Type B-06-F from Lauscha Fiber International, dimensions 0.6μ diameter, 2-3 mm long) in water. About 1.5-2 grams of microglass was mixed into 400 ml of distilled water and various quantities of nano alumina powder were added to produce different ratio's of microglass/nano alumina filters. The mixture was blended in a conventional blender at the highest setting. After preparation, the nano alumina/microglass composite was filtered by suction through a 5μ pore size filter to produce a thin fibrous mat of nano alumina and glass microfibers. The mat was separated from the coarse filter and air-dried at room temperature. One major advantage of nano alumina fibers as compared to spherical particles with equivalent surface area is that the large aspect ratios (tens to hundreds) allows them to be readily integrated into fibrous structures. The fibrous structure produces filters that are highly porous (approximately 70-80% void volume). Samples 47-52 (Table 3) were produced from nano alumina (heat treated to 400° C.) as described in Example 2 and mulched directly with glass microfibers. Nano aluminum fibers used in samples 53-62 were sieved through a 400-mesh screen to yield fibers small enough to be uniformly distributed through the filter media. The samples were tested with MS-2 as described in Example 1, and PRD-1 virus. PRD-1 is approximately 60 nanometers size and differs from MS-2 and ϕX174 in that it is more hydrophobic due to lipids in the capsid. Table 3 shows that virus retention increases with increasing percentage of nano alumina fibers. Also, the results show that better dispersion of the nano alumina (by sieving the alumina aggregates) results in about one log improvement or better in virus retention.

EXAMPLE 4

Examples 4 through 14 were formulated initially with nano aluminum powder. The nano aluminum metal was reacted with water while in the presence of a mulch of glass fibers (see Table 4 samples #63-68). About 1.5-2 grams of microglass was mixed into 400 mL of distilled water with nano aluminum. The quantity of nano aluminum varied depending on the ultimate ratio of microglass/nano alumina in the filter. The mixture was heated to 75° C. and within about 3-10 minutes the reaction became vigorous and continued for an additional 3-5 minutes. The filter was prepared as described in Example 3. Samples 69 and 70 were prepared similarly as 63-68, but were also sonicated using a Fisher ultrasonic cleaner, model FS20, during the aluminum digestion. In a variant of this process, the nano alumina sol was formed without removing the particles from the mother liquor. Microglass was subsequently added to the mulch (samples #71 and 73). The challenge virus concentration was $5 \times 10^4$ pfu/mL in buffered pH 7.5 water at a flow velocity through the filter of 1 cm/sec for samples 63-68, and 0.5 cm/sec for samples 71 and 73. When nano aluminum was digested in the presence of microglass rather than subsequent mixing, the filter had a high flow rate.

TABLE 3

Virus Test of Nano Alumina/Glass Microfiber Filter Mats

| Sample # | Aluminum Powder Form | Thickness, mm | Weight % fibers | % removal, MS-2 | % removal, PRD-1 |
|---|---|---|---|---|---|
| 51 | As-produced Nano-alumina | 2.3 | 20 | 48 | 22 |
| 52 | As-produced Nano-alumina | 1.8 | 20 | 44 | 30 |
| 47 | As-produced Nano-alumina | 1.7 | 60 | 45 | 50 |
| 48 | As-produced Nano-alumina | 2.3 | 60 | 93 | 48 |
| 49 | As-produced Nano-alumina | 1.8 | 70 | 95 | 92 |
| 50 | As-produced Nano-alumina | 1.8 | 70 | 97 | 95 |
| 53 | As-produced Nano-alumina sieved through 400 mesh | 1.3 | 40 | 48 | 20 |
| 54 | As-produced Nano-alumina sieved through 400 mesh | 1.7 | 40 | 32 | 17 |
| 55 | As-produced Nano-alumina sieved through 400 mesh | 1.8 | 50 | 75 | 47 |
| 56 | As-produced Nano-alumina sieved through 400 mesh | 2.0 | 50 | 66 | 53 |
| 57 | As-produced Nano-alumina sieved through 400 mesh | 2.0 | 60 | 99.0 | 98 |
| 58 | As-produced Nano-alumina sieved through 400 mesh | 2.0 | 60 | 99.1 | 95 |
| 59 | As-produced Nano-alumina sieved through 400 mesh | 1.9 | 70 | 99.5 | 99.1 |
| 60 | As-produced Nano-alumina sieved through 400 mesh | 2.0 | 70 | 99.4 | 99.0 |
| 61 | As-produced Nano-alumina sieved through 400 mesh | 2.9 | 80 | >99.9 | 99.7 |
| 62 | As-produced Nano-alumina sieved through 400 mesh | 2.7 | 80 | >99.9 | 99.9 |

Examples 5-14 utilized the concurrent reaction of nano aluminum in the presence of microglass.

Figure 3:
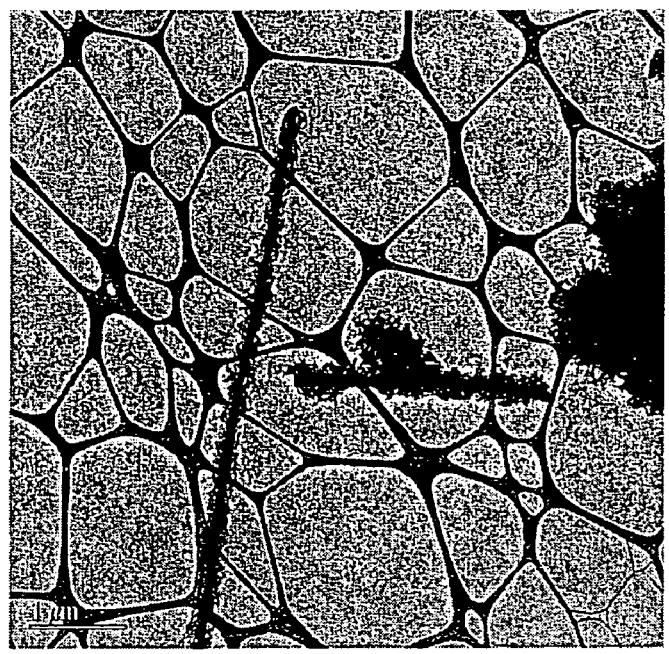
FIG. 3 is a micrograph of nano alumina/Microglass composite.

Referring now to FIG. 3, samples of freshly prepared filters were examined by transmission electron microscopy. The nano alumina fibers shown are combined as aggregates, or are dispersed and attached to the surface of microglass fibers. Such dispersal is likely responsible for the improved virus retention over the samples prepared as in Table 3.

TABLE 4

Virus Retention of Mixed Nano alumina/Microglass Filters

| Sample # | Method | Thickness, mm | Weight % Fibers | MS-2, % removal | PRD-1 % Removal |
|---|---|---|---|---|---|
| 63 | React nano aluminum in the presence of glass fibers | 1.1 | 40 | >99.993 | >99.997 |
| 64 | React nano aluminum in the presence of glass fibers | 1.2 | 40 | >99.993 | >99.997 |
| 65 | React nano aluminum in the presence of glass fibers | 1.3 | 50 | >99.993 | >99.997 |
| 66 | React nano aluminum in the presence of glass fibers | 1.5 | 50 | >99.993 | >99.997 |
| 67 | React nano aluminum in the presence of glass fibers | 1.1 | 60 | >99.993 | >99.997 |
| 68 | React nano aluminum in the presence of glass fibers | 2.0 | 60 | >99.993 | >99.997 |
| 69 | As above with sonication | 1.2 | 60 | >99.993 | >99.997 |
| 70 | " | 1.3 | 60 | >99.993 | >99.997 |
| 71 | Mix Alumina sol and glass Fibers | 1.0 | 40 | >99.993 | >99.997 |
| 73 | Mix Alumina sol and glass Fibers | 0.8 | 60 | >99.993 | >99.997 |

EXAMPLE 5

Figure 4:
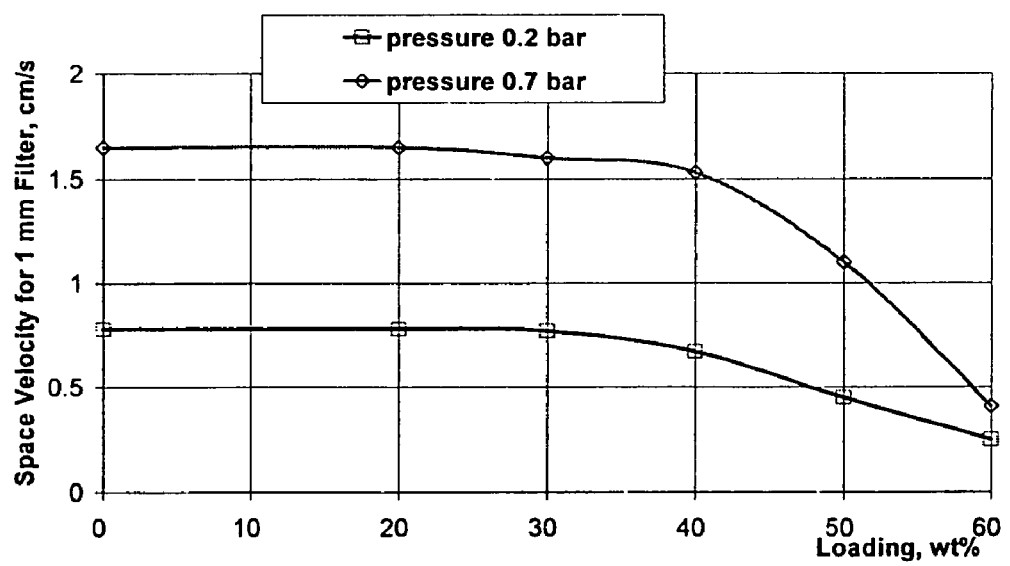
FIG. 4 is a graphical depiction of water flow velocity through nano alumina filters 1 mm thick, 25 mm diameter.

Referring now to FIG. 4, 25 mm diameter, 1 mm thick nano alumina filters were prepared as in Example 4. These were tested for water flow rate at applied pressures of 0.2 and 0.7 atmospheres (0.2 and 0.7 bar). FIG. 4 illustrates that the linear flow (space) velocity at 0.7 bar was roughly constant at 1.6 cm/sec for loadings up to about 40 weight percent (wt %) nano alumina. This flow rate is substantially greater, roughly 2 orders of magnitude, as compared to ultra porous membranes. The flow velocity claimed by Millipore for their VS ultra porous filters (25 nm pore size) is only 0.0025 cm/s at an applied pressure of 0.7 bar, about 660 times lower than the present example. Generally the flow rates of membrane filters suitable for virus retention range from about of 300-600 L/m$^2$/hr. Nano alumina filters achieve high retentivity for viruses as small as 30 nanometers in size at flow rates between about 10,000 and 20,000 L/m$^2$/hr.

The reason for the high flow is the increased porosity of the nano alumina filter. Up to about 40 wt %, the nano alumina is principally attached to the microglass and causes little flow impedance. An additional factor is the filter's hydrophilic character. Membranes composed of cellulose esters, plastics, and PTFE are generally hydrophobic. Water can be forced through hydrophobic filters; however, the pressure required to force water through pores smaller than 1 µm increases rapidly with reduction in pore size, thus resulting in a drastic pressure drop. Furthermore, and the risk of uneven wetting increases. Often membranes are treated with wetting agents, such as glycerol, Tween, and Triton X-100, to facilitate flow. Such wetting agents may subsequently interfere in processing of special products such as pharmaceuticals.

EXAMPLE 6

The intent of this series was to determine the maximum attainable removal efficiency of virus. Example 4 illustrated that the virus challenge concentration was insufficient to distinguish any variations and it was therefore increased to 1×10$^7$ pfu/mL. The following experiments (Table 5) were performed in buffered pH 7.5 water at a flow velocity of 1 cm/sec. Virus retention >6 logs (>99.9999%) was achieved starting at approximately 20 wt % nano alumina loading. When all samples tested in sequence showed >6 logs, filters with <20 wt % were prepared and tested (samples 113-120). The data illustrate increasing retention with loading up to about 20 wt %. Any further testing of the virus assay technique is limited by the difficulty of producing virus challenge streams >10$^7$ pfu/mL. The data suggest that virus retention for 30-60% nanoalumina loadings would be substantially greater than the values shown in Table 5.

TABLE 5

Virus Removal for nano alumina Filters

| Sample # | Thickness, mm | Weight % nano alumina | MS-2 % removal | PRD-1 % removal |
|---|---|---|---|---|
| 113 | 1.0 | 0 | Dissolved | |
| 114 | 1.2 | 0 | 8 | |
| 115 | 0.8 | 2 | 12 | |
| 116 | 1.4 | 2 | 16 | |
| 117 | 1.0 | 5 | 30 | |
| 118 | 1.0 | 5 | 28 | |
| 119 | 1.2 | 10 | 89 | |
| 120 | 0.9 | 10 | 98 | |
| 85 | 1.1 | 20 | >99.9999 | >99.99999 |
| 86 | 1.1 | 20 | >99.9999 | 99.99999 |
| 87 | 1.3 | 30 | >99.9999 | >99.99999 |
| 88 | 1.4 | 30 | >99.9999 | 99.99999 |
| 89 | 1.3 | 40 | >99.9999 | 99.9998 |
| 90 | 1.3 | 40 | >99.9999 | 99.99991 |
| 91 | 1.2 | 50 | >99.9999 | >99.99999 |
| 92 | 1.5 | 50 | >99.9999 | 99.99999 |
| 93 | 1.5 | 60 | >99.9999 | >99.99999 |
| 94 | 1.3 | 60 | >99.9999 | 99.99999 |

TABLE 5-continued

Virus Removal for nano alumina Filters

| Sample # | Thickness, mm | Weight % nano alumina | MS-2 % removal | PRD-1 % removal |
|---|---|---|---|---|
| 95 | 1.5 | 70 | >99.9999 | 99.99999 |
| 96 | 1.2 | 70 | >99.9999 | 99.99999 |

EXAMPLE 7

The purpose of this series was to measure the retention of bacteria (*E. coli* O157H7) and viruses (MS-2 and polio) in the presence of simulated seawater or sewage effluent. Filter samples (Table 6) were prepared as in Example 4. An artificial seawater environment (samples #135, 136) shows little or no change in virus or bacteria retention as compared to the control (samples #131, 132) demonstrating that the filter is effective in salty or brackish water. The data also indicate that nano alumina filters could be used as pre-filters to minimize the clogging of reverse osmosis membranes used in desalination. The sewage challenge mixture was prepared from sewage, passed through a 100μ filter and then spiked simultaneously with viruses and *E. coli* before being passed through the test filter. No difference in retention was noted between the sewage challenge and the buffered control indicating that the filter could remove microbes and virus from sewage contaminated water.

TABLE 6

Retention of Viruses and Bacteria from Salt and Sewage Water

| Sample # | Weight % fibers | Thickness, mm | Adsorption experiment performed in[1] | % removal *E. coli* O157H7[4] | % removal MS2 | % removal Polio |
|---|---|---|---|---|---|---|
| 131 | 40 | 1.4 | Buffer pH 7.4 | >99.99 | >99.999 | 99.92 |
| 132 | 40 | 1.6 | Buffer pH 7.4 | >99.99 | >99.999 | 99.97 |
| 133 | 40 | 1.8 | Sewage[2] | >99.99 | >99.999 | >99.99 |
| 134 | 40 | 1.7 | Sewage | >99.99 | >99.999 | 99.99 |
| 135 | 40 | 1.6 | Artificial Sea[3] Water pH 7.8 | >99.99 | >99.999 | >99.99 |
| 136 | 40 | 1.4 | Artificial Sea Water pH 7.8 | >99.99 | >99.999 | >99.99 |

[1]Buffer consisted of 0.02 M Glycine and 0.02 M immidizole adjusted to pH 7.4.—Initial titer of pathogen >$10^5$ pfu/mL
[2]Sewage from University of Florida wastewater treatment facility and filtered through a 100 micron filter
[3]Commercial marine salt mix (Instant Ocean ®), adjusted to pH 7.8.
[4]*E. coli* O157H7 was made Rifampicin resistant and assayed by inoculating Tryptic Soy agar Plates supplemented with 0.1 g Rifampicin/1000 mL.

Table 6 results illustrate that bacteria can be retained on nano alumina filter media. DiCosmo found that glass fiber mats would effectively immobilize a biomass of *Catharanthus roseus*. Adding nano alumina further enhances the immobilization, and such composite mats can be used as a substrate for harvesting and proliferating bacteria for the purposes of biosynthesis. Co-pending U.S. Patent Application Ser. No. 60/324,398 (filed Sep. 24, 2001 by Purdue Univ), demonstrates that osteoblast (bone cells) adhere to nano alumina fibers and proliferate on them demonstrating that nano alumina fiber mats would be an effective substrate for the growth of mammalian cells.

EXAMPLE 8

The purpose of this example (Table 7) determined the feasibility of collecting live virus from a sample for subsequent assay. All samples were composed of 40 wt % nano alumina fibers with microglass prepared as described in Example 4. The filters were challenged in a virus solution of at least 1×$10^5$ pfu/mL in buffered pH 7.5 water as described in example 4. After passing 10 mL of virus spiked solution through the filter, a solution of 10 mL of 1.5% beef liver extract and 0.25% glycine at pH 9.3 was flowed through the filter counter current to the adsorption direction. The results indicate that live virus can be displaced from nano alumina filters for the purpose of biological assay.

TABLE 7

Retention/Elution of MS-2 and Polio Viruses

| Sample # | Thickness, mm | Challenge Solution | MS-2 % removal | MS-2 % elution[1] | Polio 1 % removal | Polio 1 % elution[1] |
|---|---|---|---|---|---|---|
| 173 | 1.6 | Instant Ocean | 99.95 | 75 | 99.9 | 55 |
| 174 | 1.4 | Instant Ocean | 99.995 | 79 | 99.98 | 81 |
| 175 | 1.4 | Instant Ocean | 99.994 | 81 | 99.99 | 75 |
| 176 | 1.4 | Instant Ocean | >99.999 | 73 | 99.95 | 59 |
| 177 | 1.5 | Sewage | 99.99 | 96 | 99.95 | 81 |
| 178 | 1.6 | Sewage | 99.993 | 98 | 99.992 | 75 |
| 179 | 1.5 | Sewage | 99.998 | 95 | 99.993 | 80 |
| 180 | 1.4 | Sewage | 99.98 | 97 | 99.98 | 89 |

The filter can be regenerated by several modes non-exclusively including:

A. increasing the pH of the elutant until the filter has a zero or negative charge.
B. eluting with a macromolecule such as beef liver extract, more preferably adsorbed than the particle it would replace;
C. drying and/or heating the filter media to drive off bulk and adsorbed water, destroying ionic charges that contribute to the electrostatic charge. The filter is dried at temperatures while still preserving the viability of the pathogens for subsequent assay, or higher to kill the pathogen in place. Both the nano alumina as well as the microglass of the filter media are thermally stable to temperatures greater than about 300° C., where bacteria and virus are completely destroyed; or
D. electrochemically regenerating the filter. A negative electrode can be incorporated as part of the filter to generate negative ions and displace adsorbed particles. The electrode is composed of a stainless steel screen electrode embedded in the filter, along with graphite flake or preferably carbon (graphitized) fiber. At least 5 volume percent graphite is incorporated into the filter assembly to enhance electronic conductivity. A positive current collector, constructed of a metal that is essentially inert to electro-oxidation such as stainless steel, tungsten or tantalum is located outside of the filter media. After the adsorption cycle, the filter is electrochemically regenerated by liquid flowing through the filter counter to the direction of the adsorption cycle, resulting in displacement of the adsorbed particle by negative ions.

EXAMPLE 9

Figure 5:
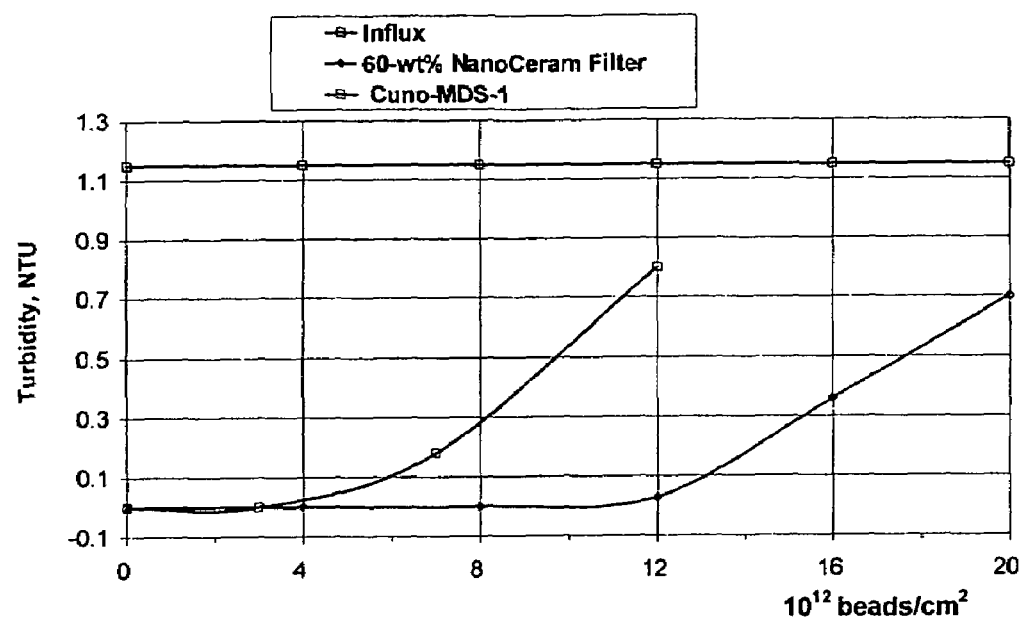
FIG. 5 is a graphical depiction illustrating the breakthrough of 30 nm latex beads through 25 mm filters.

Referring now to FIG. 5, the purpose of this example was to measure the particle capacity of filters by challenging the filters, (with 30 nanometer diameter monodisperse latex beads (Duke Scientific Corp) using procedures defined by Hou. The filters were prepared as in Example 4. An optical turbidimeter (LaMotte Model 2020) was used to measure the turbidity that developed as beads leaked into the effluent. The challenge solution was distilled water containing latex beads with particle density of $10^{12}$/mL. We tested 25 mm diameter filters (effective surface area ~5 cm$^2$) at a constant flowrate, comparing Cuno MDS-1 filter media vs. nano alumina. The nano alumina filters were backed by a 5μ pore membrane to intercept any shedding of glass microfibers into the fitrate. This sandwich was tightened with O-rings to avoid a bypass of the influent solution outside the filtration area. FIG. 5 illustrates the breakthrough curves for the two types of filters. The units on the x-axis represent the total amount of latex beads in the challenge mixture per square centimeter (cm$^2$) of filter area. These data indicate that the sorption capacity (the point at which some turbidity first appears) of nano alumina filters for 30 nm particles is about 3 times greater than the Cuno filter.

EXAMPLE 10

Figure 6:
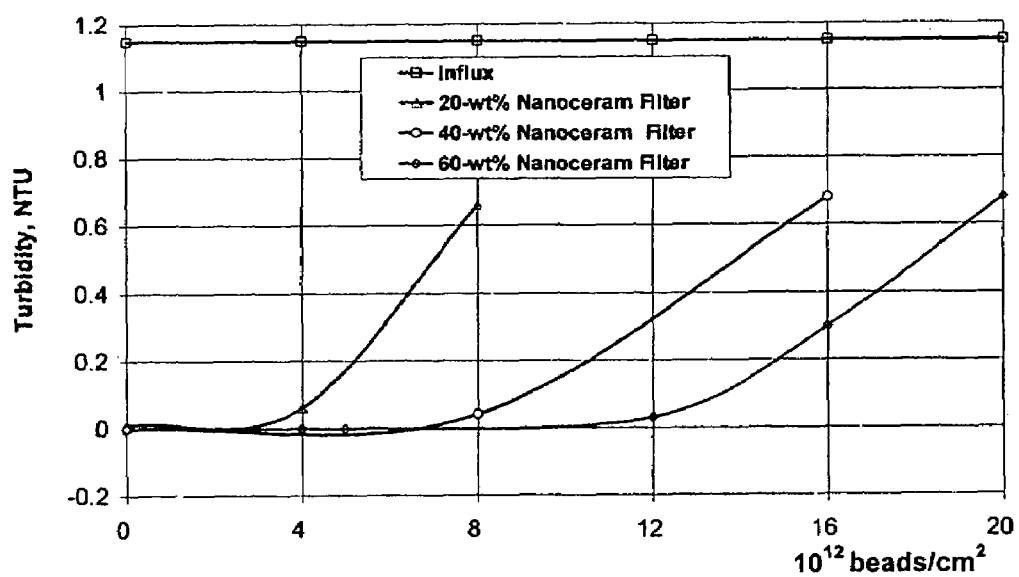
FIG. 6 is a graphical depiction illustrating the breakthrough curves (30 nm latex beads) as function of weight percent nano alumina fiber.

Referring now to FIG. 6, tests compare the sorption capacity of filters for 30 nm latex beads as a function of nano alumina loading. 30 nm latex beads simulate the adsorption of virus. The capacity is almost directly proportional to the loading of nano alumina fibers in the filter. The ability to increase capacity by increasing thickness is a major advantage over that of membranes. Doubling the thickness of a nano alumina filter doubles the capacity at the cost of halving the flow rate while doubling thickness of a membrane would clog more rapidly without increasing capacity or retention capability. The initial virus retention of the thicker filter is substantially greater than 7 logs.

The breakthrough waveforms exhibited in FIGS. 5 and 6 are typical of adsorption curves in liquid chromatography columns, with the exception that adsorption in this case is primarily the result of opposite electrostatic charges on the sorbent and particle. Therefore, a stack of nano alumina filters are an effective column for separating virus and other macromolecules on the basis of their charge.

Figure 7:
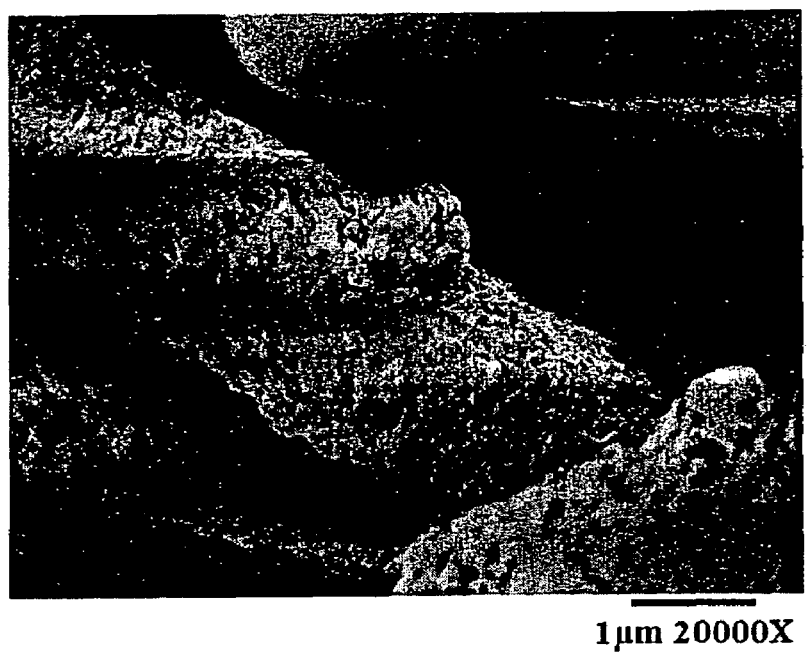
FIG. 7 is a scanning electron micrograph of nano alumina filter saturated with 30 nm latex beads.

Referring now to FIG. 7, which is a scanning electron microscope micrograph of a microglass fiber extracted from a nano alumina filter loaded with 30 nm latex beads beyond breakthrough. Note the microglass was completely covered by a layer of latex, while there does not appear to be loose or partially adherent beads. This illustrates that the beads are held tightly to the microglass fiber.

EXAMPLE 11

Figure 8:
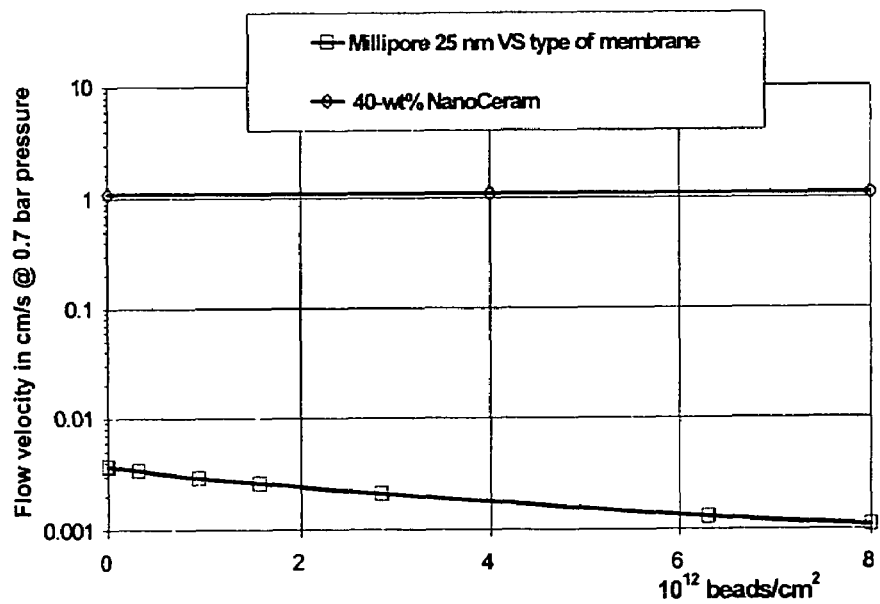
FIG. 8 is a graphical depiction illustrating the flow rate decay resulting from loading by 30 nm latex beads.

Referring now to FIG. 8, flow rate decay, an index of clogging resistance of the filter, was measured for nano alumina versus a 25 nm pore size membrane (Millipore VS). The challenge solution was distilled water loaded with 30 nm beads again to a density of $10^{12}$ beads/mL. The applied pressure on both filters was 0.7 atmosphere (0.7 bar). The nano alumina filter was prepared as in Example 4 and was 1 mm thick and had 40 wt % nano alumina fibers. There was no discernable loss in flowrate in the case of nano alumina to its breakpoint ($8\times10^{12}$ beads/cm$^2$) while the membrane lost 70% of its flow capability during the same interval, presumably due to clogging of its surface by the latex beads. At the point of breakthrough, the flow through nano alumina was about 3 orders of magnitude greater than the ultraporous membrane. The lack of decay of the nano alumina is due to the relatively small impact the adsorbed latex particles have upon reducing the cross-sectional area of the pores in the filter.

EXAMPLE 12

Figure 9:
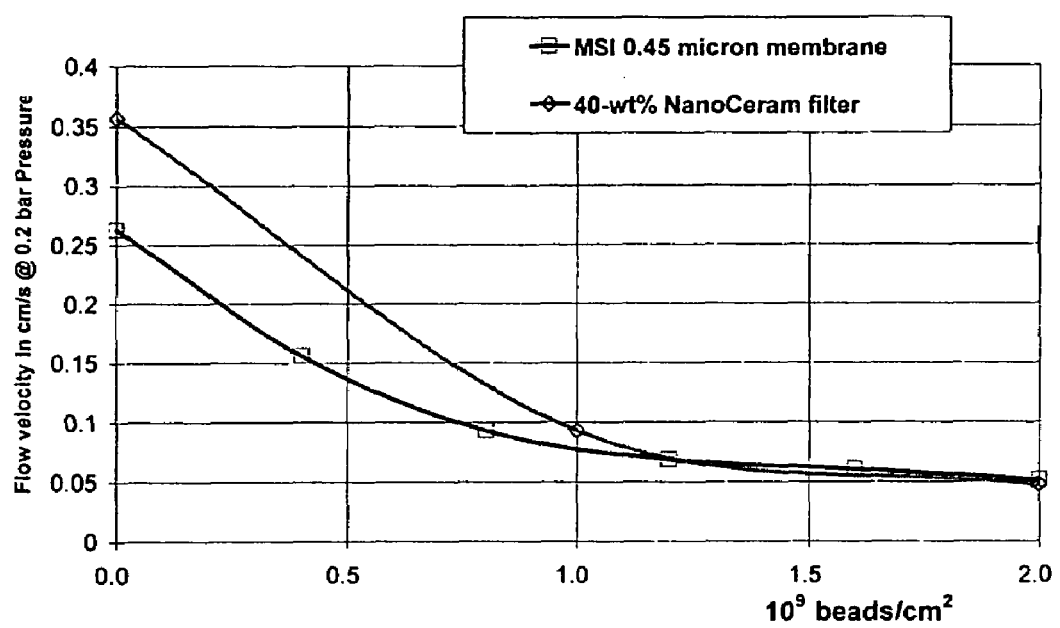
FIG. 9 is a graphical depiction illustrating the flow decay by accumulation of 3μ latex beads.

Example 11 was repeated but with 3 micron diameter latex beads, comparing the 40 wt % nano alumina filter to a 0.45μ pore (Millipore-HA) membrane. The object of the experiment was to determine relative flow decay when the filters were challenged by particles simulating the size of bacteria and protozoa. FIG. 9 indicates that the flow decay pattern of nano alumina was similar to the 0.45μ pore membrane. Flow velocity through the nano alumina decayed until it matched that of the membrane. It appears that micron size particles are collected (sieved) on the surface of the two filters and after some accumulation; the flow is controlled by the thickness of the filter cake as well as its porosity. This was confirmed by observing a layer of latex that could be peeled from on the surface of both filters while there was no evidence of latex film after loading nano alumina with 30 nm diameter latex beads (see FIGS. 5-8). FIG. 9 illustrates that 40 wt % nano alumina produced in accordance with Example 4 will filter bacteria size particles by size exclusion rather than electrostatic adsorption, as is the case with virus-size particles. However nano alumina media can be optimized for electrostatic adsorption of bacteria size particles by increasing the porosity and therefore the nominal pore size of the filter. Such an increase in porosity can be achieved by adding larger diameter fibers to the mulch. Further, a layer optimized for virus retention can back a filter layer optimized for micron size particles. The net effect of such "graded" filters would be less clogging, higher flow rates, and longer filter life before requiring replacement or regeneration.

EXAMPLE 12

A sol of boehmite nanofibers was produced by reacting 5 diameter aluminum powder (Valimet Corp. #H-5) in water at 100° C. while in the presence of a mulch of glass fibers. The filters were prepared and tested as in Example 4 with an MS-2 challenge concentration of $1\times10^7$ pfu/mL. The data indicate equivalent virus retention to filters produced from nanosize aluminum powder. Another variant of nano alumina fibers was prepared by hydrothermal reaction of aluminum trihydroxide with ammonium hydroxide ($NH_4OH$). A mixture of about 6 grams of microglass fiber, 5.2 grams of $Al(OH)_3$, and 1 mL of 30% $NH_4OH$ in 100 mL of water was heated to about 170° C. (steam pressure about 10 bar) for 2 hours. After cooling the powder was filtered and filter media prepared as in samples 63-68 in Example 4. The data of Table 8 illustrate >99.9% virus retention for 2 mm thick filters produced from the above reaction.

TABLE 8

Virus Retention of nano alumina Filters Prepared by Alternate Routes

| Sample # | Method | Thickness (mm) | Weight % fibers | MS-2 Removal (%) |
|---|---|---|---|---|
| 123 | Coarse (5µ) Aluminum particles digested with glass fibers | 1.0 | 40 | >99.9999 |
| 124 | Coarse (5µ) Aluminum particles digested with glass fibers | 1.4 | 40 | >99.9999 |
| 259 | Reaction of Al(OH)$_3$ in water at 170° C. and 10 bar pressure | 2.0 | 40 | >99.9 |

EXAMPLE 13

A three-layer laminated filter comprised of outer layers of cellulose (cotton linter pulp GR 505 from Buckeye Cellulose Corp) approximately 0.2 mm thick, and an internal core layer of 40% nano alumina/microglass approximately 1.2 mm thick. In the first step a mulch of cellulose was formulated as described in Example 4 and then poured into a Buchner funnel with a #5 filter producing a first cellulosic layer. While still moist, a mulch of nano alumina/microglass fibers was poured on top of the first layer. After one hour drying, an additional layer of cellulose mulch was poured onto the intermediate layer. While the nano alumina/microglass composite has poor dry and wet strength, the laminated structure was much more resistant to tearing in both the dry and wet condition, providing a more rugged structure for industrial and laboratory use.

EXAMPLE 14

A structure similar to Example 13 was formed, wherein fusible porous organic tape (Singer Sewing Co. Fusing Tape) was substituted for the cellulose outer layers. The resulting composite has stronger tear resistance than that of Example 12. Water flow characteristics are very similar to that of samples prepared as in Example 4.

EXAMPLE 15

A plastic non-woven fabric (Delnet P620, Delstar Technologies, Middletown, Del.) was used to cover a tubular plastic screen filter core 1.325 inches in diameter by 8.4375 inches in length. The filter was closed off at a first end and a vacuum fitting attached at the second end. A vacuum line was attached to the vacuum fitting and the assembly immersed in a mixture of approx. 2 liters of distilled water blended with 3.7 g of glass micro fiber and 2.5 g of nano alumina fibers. Vacuum was applied to center axis of the immersed filter. The glass micro fiber and nano alumina particles deposited on the surface of the filter core. After air drying, a coating of mixed fibers deposited over the non-woven fabric at a thickness of about 1 mm and a total surface area of about 35 in$^2$.

Other modifications of nano alumina media can be formulated that would increase strength and reduce the shedding of fibrous components into process water streams, nonexclusively including:

A. adding a silane such as trimethoxyl silane to the mulch;
B. adding a longer or stronger fiber such as cellulose chopped melt blown polymer to the nano alumina/Microglass core mulch;
C. adding a thermoplastic fiber to the nano alumina/microglass core mulch that could be heat fused or glued to bond the fibrous components after the web is dried;
D. depositing the nano alumina onto a web of cellulose plastic or metal screen;
E. laminating the wet laid nano alumina core discs between webs of thermoplastic fibers and partially fuse the composite;
F. adding bonding agents including starch or polyacrylamides that would strengthen the nano alumina core by hydrogen bonding; or
G. adding a wet strength adhesive such as urea-formaldehyde or melamine-formaldehyde thermosetting resins to the nano alumina core.

Filter media sheets in accordance with the invention may be employed alone or in combination with other such media to remove sub-micron and nanosize particulates from liquids, including the sterilization of water from viruses, to treat pharmaceuticals such as antibiotics, saline solutions, dextrose solutions, vaccines, blood plasma, serums, beverage purification such as wines and spirits, cosmetics such as mouthwash, food products such as fruit juices, chemicals such as antiseptics, photographic solutions, cleaning solutions, solvent purification and the like for removal of sub micron particles and macromolecules such as pyrogens and endotoxins, particularly from parenteral solutions.

Such media may also be used to collect and sample microbial pathogens for the purpose of detection and analysis.

Alumina fiber media may also be utilized in the separation of two macromolecules, such as proteins, as a result of differences in their adhesion to the nano alumina surface. This can be done either by chromatography based on charge differences of the two macromolecules or in the presence of an electric field (electrophoresis)

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

| Patents Cited | | | Class |
|---|---|---|---|
| 2,783,894 | March 1957 | Lovell et al. | 210/500.38 |
| 2,915,475 | December 1959 | Bugash | 516/94 |
| 3,031,417 | April 1962 | Bruce | 516/94 |
| 3,408,315 | October 1968 | Payne | 264/49 |
| 3,242,073 | March 1966 | Guebert | 210/64 |
| 3,352,424 | November 1967 | Guebert | 502/62 |
| 3,947,562 | March 1976 | Grimshaw | 423/630 |
| 4,007,113 | February 1977 | Ostreicher | 210/504 |
| 4,007,114 | February 1977 | Ostreicher | 210/504 |
| 4,178,438 | December 1979 | Haase et al. | 536/30 |
| 4,230,573 | October 1980 | Kilty et al. | 210/767 |
| 4,282,261 | August 1981 | Greene | 426/330.4 |
| 4,288,462 | September 1981 | Hou et al. | 426/423 |
| 4,305,782 | December 1981 | Ostreicher et al. | 162/181.6 |
| 4,309,247 | January 1982 | Hou et al. | 162/149 |
| 4,321,288 | March 1982 | Ostreicher | 427/244 |
| 4,331,631 | May 1982 | Chapman | 422/180 |
| 4,366,068 | December 1982 | Ostreicher et al. | 210/767 |
| 4,473,474 | August 1984 | Ostreicher et al. | 210/636 |

-continued

| Patents Cited | | | Class |
|---|---|---|---|
| 4,523,995 | June 1985 | Pall et al. | 210/504 |
| 4,604,208 | August 1986 | Chou et al. | 210/636 |
| 4,617,128 | October 1986 | Ostreicher | 210/679 |
| 4,673,504 | June 1987 | Ostreicher et al. | 210/500.22 |
| 4,708,803 | November 1987 | Ostreicher et al. | 210/650 |
| 4,711,793 | December 1987 | Ostreicher et al. | 427/244 |
| 4,743,418 | May 1988 | Barnes, et al. | 264/48 |
| 5,085,784 | February 1992 | Ostreicher | 210/767 |
| 5,104,546 | April 1992 | Filson, et al | 210/650 |
| 5,219,577 | June 1993 | Kossovsky et al | 424/494 |
| 5,798,220 | August 1998 | Kossovsky et al | 435/13 |
| 5,855,788 | January 1999 | Everhart, et al. | 210/653 |
| 6,197,515 | March 2001 | Bamdad et al | 435/6 |

REFERENCES CITED

Ahuja, S, (2000) Handbook of Bioseparations—Academic Press.

DiCosmo, et al., (1994)—Cell Immobilization by Adsorption to Glass Fibre Mats—in Immobilized Biosystems, Edited by Veliky, I. A. and McLean, R. J. C.—Blackie Academic & Professional.

Farrah, S. R. and Preston, D. R., (December 1985) Concentration of Viruses from Water by Using Cellulose Filters Modified by In-situ Precipitation of Ferric and Aluminum Hydroxides, Applied and Environmental Microbiology, 1502-04.

Farrah, S. R. and Preston D. R. (1991) Adsorption of Viruses by Diatomaceous Earth Coated with Metallic Oxides and Metallic Peroxides, Water Sci. Tech., V. 24: 2, 235-40.

Gitzen, W. H., (1970) Alumina as a Ceramic Material, American Ceramic Soc., Special publication 4, pp. 13-14

Hou, K. et al. (November 1980), Capture of Latex Beads, Bacteria, Endotoxin and Viruses by Charge-Modified Filters, Appl. And Environmental Microbiology, 892-96.

Khalil, Kamal M. S., (1998), Journal of Catalysis, 178, 198-206.

Lukasik, J., et al., Influence of Salts on virus Adsorption to Microporous Filters—Appl. Environ. Micro. 66:2914-40 (Lukasik I).

Lukasik, J., et al. (1999). Removal of Microorganisms from Water by Columns Containing Sand Coated with Ferric and Aluminum Hydroxides, Wat Res. 33: 3, 769-77, (Lukasik II).

Mandaro, (1987) "Charge Modified Depth Filters: Cationic-Charge Modified Nylon Membranes" in Filtration in the Pharmaceutical Industry, T. H. Meltzer Ed., Marcel Dekker, Inc., New York, N.Y.

Meltzer, T. H. and Jornitz, M. W., (1998), Filtration in the Biopharmaceutical Industry—Marcel Dekker, New York, 1998, pp. 262-265

Nycomed Applications and Products brochure, (2000) 39.

Robinson et al. (1985), "Depyrogenation by Microporous Membrane Filters", in Technical Report No. 7, Depyrogenation, Parenteral Drug Association, Inc., Phila, Pa.

Sinha, D., (1990) "Pretreatment Process Considerations for the Semiconductor Industry" in Ultrapure Water 7:6, 21-30.

Sobsey, M. D. and Jones, B. L., (March 1979), Concentration of Poliovirus from Tap water Using Positively Charged Microporous Filters—Appl and Environmental Microbiology, 588-595.

Willkommen, H., (Oct. 1-3, 2001), Virus Validation of Filtration Procedures, PDA/FDA Viral Clearance Forum, Bethesda, Md.

Yavorovsky, N. A., (1996) Izvestiia VUZ. Fizika 4:114-35.

We claim:

1. A fibrous electropositive sorbent comprising a blended mixture of non-spherical nano alumina particles comprising AlOOH blended with and a second matrix solid, wherein said electropositive sorbent adsorbs at least one electropositive particle from a fluid.

2. The electropositive sorbent of claim 1 wherein a source of said nano alumina particles is an aluminum metal powder.

3. The fibrous electropositive sorbent of claim 1 wherein a source of said nano alumina particles is aluminum hydroxide.

4. The fibrous electropositive sorbent of claim 1 wherein said non-spherical nano alumina particles are asymmetrically shaped, have a minor dimension of less than about 100 nm and an aspect ratio of length to thickness of at least 5.

5. The fibrous electropositive sorbent of claim 1 wherein said nano alumina particles have diameters less than 10 nanometers.

6. The fibrous electropositive sorbent of claim 1 wherein said second solid is a fibrous structure.

7. The fibrous electropositive sorbent of claim 6 wherein said fibrous structure comprises glass fibers.

8. The fibrous electropositive sorbent of claim 1 wherein said second solid is arranged to form a plurality of pores, each pore having an average size of about 3 μm.

* * * * *

UNITED STATES PATENT AND TRADEMARK OFFICE
CERTIFICATE OF CORRECTION

PATENT NO.       : 7,601,262 B1
APPLICATION NO.  : 11/023281
DATED            : October 13, 2009
INVENTOR(S)      : Frederick Tepper and Leonid Kaledin It is certified that error appears in the above-identified patent and that said Letters Patent is hereby corrected as shown below:

Column 24, Line 27 should read "electropositive sorbent absorbs at least one electronegative".

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,262 B1 | Page 1 of 1 |
| APPLICATION NO. | : 11/023281 | |
| DATED | : October 13, 2009 | |
| INVENTOR(S) | : Frederick Tepper and Leonid Kaledin | |

It is certified that error appears in the above-identified patent and that said Letters Patent is hereby corrected as shown below:

Column 24, Line 27 should read "electropositive sorbent at least one electronegative".

This certificate supersedes the Certificate of Correction issued November 16, 2010.

Signed and Sealed this
Fourth Day of January, 2011

David J. Kappos
*Director of the United States Patent and Trademark Office*